United States Patent
Ishikawa et al.

(10) Patent No.: US 7,834,183 B2
(45) Date of Patent: Nov. 16, 2010

(54) PROCESS FOR PRODUCING N-(HETERO)ARYL-SUBSTITUTED NITROGEN-CONTAINING HETEROARYL COMPOUND

(75) Inventors: Yuji Ishikawa, Kanagawa (JP); Susumu Harada, Kanagawa (JP); Ken Umihara, Kanagawa (JP)

(73) Assignee: Fujifilm Finechemicals Co., Ltd, Tokyo (JP)

( * ) Notice: Subject to any disclaimer, the term of this patent is extended or adjusted under 35 U.S.C. 154(b) by 476 days.

(21) Appl. No.: 11/635,664

(22) Filed: Dec. 8, 2006

(65) Prior Publication Data

US 2007/0135633 A1 Jun. 14, 2007

(30) Foreign Application Priority Data

Dec. 9, 2005 (JP) ............................. 2005-356876

(51) Int. Cl.
C07D 213/00 (2006.01)
(52) U.S. Cl. ........................................................ 546/1
(58) Field of Classification Search ................... None
See application file for complete search history.

(56) References Cited

U.S. PATENT DOCUMENTS 6,815,390 B2 * 11/2004 Vaughan et al. ............. 502/150

2004/0002507 A1 1/2004 Nagarathnam et al.
2005/0054631 A1 3/2005 Jiang et al.

OTHER PUBLICATIONS

Liu et al. Bioorganic and Medicinal Chemistry Letters, 2005, 15, 2437-40.*
Romero et al. Tetrahedron, 2006, 62, 9010-16.*
Hartwig et al. Journal of Organic Chemistry, 1999, 64, 5575-80.*
Lysen et al. Synthesis, 2006, 4, available online Jan. 19, 2006.*
Lysen et al. Synlett, 2005, 11, 1671-74.*
March. Advanced Organic Chemistry, 1994, p. 250.*
Efficient Palladium-Catalyzed N-Arylation of Indoles, Department of Chemistry, Massachusetts Institute of Technology Cambridge, Massachusetts 02139, David W. Old, Michelle C. Harris, and Stephen L. Buchwald, Organic Letters 2000 Vo. 2, No. 10 1403-1406.

* cited by examiner

*Primary Examiner*—James O Wilson
*Assistant Examiner*—Noble Jarrell
(74) *Attorney, Agent, or Firm*—Sughrue Mion, PLLC

(57) ABSTRACT

A process for producing an N-(hetero)aryl-substituted nitrogen-containing heteroaryl compound, the process comprising: reacting a heteroaryl compound having an NH group as a ring-constituting component with a (hetero)aryl compound having a leaving group in the presence of a heterogeneous-system platinum group metal catalyst, a ligand and a base.

6 Claims, No Drawings

US 7,834,183 B2

PROCESS FOR PRODUCING N-(HETERO)ARYL-SUBSTITUTED NITROGEN-CONTAINING HETEROARYL COMPOUND

BACKGROUND OF THE INVENTION

1. Field of the Invention

The present invention relates to a process for producing an N-(hetero)aryl-substituted nitrogen-containing heteroaryl compound which is useful in the fields of medicines, agricultural chemicals, organic electroluminescent elements, catalyst ligands, solar cell elements, etc.

2. Description of the Related Art

N-(Hetero)aryl-substituted nitrogen-containing heteroaryl compounds are important intermediates for medicines and agricultural chemicals and are useful intermediates for organic electroluminescent elements, catalyst ligands, solar cell elements, and the like. Especially in the field of medicines, the compounds are exceedingly useful as intermediates for medicines for depression, cardiovascular diseases, inflammatory diseases, and other diseases (see International Publication No. 2003/104222, pamphlet, International Publication No. 2003/4027, pamphlet and European Patent No. 580502).

A known method for synthesizing an N-(hetero)aryl-substituted nitrogen-containing heteroaryl compound is a method of N—C bond formation by the Ullmann reaction employing a combination of a copper powder or copper salt and various ligands (see International Publication No. 2003/104222, pamphlet and Journal of the American Chemical Society, 2002, Vol. 124, No. 39, pp.11684-11688). However, this method has had drawbacks, for example, that impurities generate considerably due to the high-temperature reaction and a complicated purification operation is necessary for removing these impurities and that the reaction requires much time.

Another method which has been disclosed is a process for production in a homogeneous system employing a palladium catalyst and a phosphine ligand (see U.S. Patent Application Publication No. 2005054631 and Organic Letters, 2000, Vol. 2, pp. 1403-1406). However, this process has had drawbacks that since the catalyst is unstable in air, it is necessary to strictly remove oxygen from the reaction system and that the catalyst is difficult to recover/reuse, resulting in an exceedingly high production cost.

SUMMARY OF THE INVENTION

An object of the invention is to provide a process by which an N-(hetero)aryl-substituted nitrogen-containing heteroaryl compound useful in the fields of medicines, agricultural chemicals, organic electroluminescent elements, catalyst ligands, solar cell elements, etc. can be produced on an industrial scale in high yield at low cost.

The present inventors made intensive investigations in order to accomplish that object. As a result, they have found that the object can be accomplished with a novel method of synthesizing an N-(hetero)aryl-substituted nitrogen-containing heteroaryl compound. The invention has been thus completed. Namely, the invention is achieved with the following methods.

<1> A process for producing an N-(hetero)aryl-substituted nitrogen-containing heteroaryl compound, the process comprising:

reacting a heteroaryl compound having an NH group as a ring-constituting component with a (hetero)aryl compound having a leaving group in the presence of a heterogeneous-system platinum group metal catalyst, a ligand and a base.

<2> The process for producing an N-(hetero)aryl-substituted nitrogen-containing heteroaryl compound as described in <1> above, wherein the heteroaryl compound having an NH group as a ring-constituting component is pyrrole, indole, pyrazole, indazole, imidazole, benzimidazole, triazole or benzotriazole which each may have one or more substituents.

<3> The process for producing an N-(hetero)aryl-substituted nitrogen-containing heteroaryl compound as described in <1> above, wherein the heteroaryl compound having an NH group as a ring-constituting component is pyrrole, indole, imidazole or benzimidazole which each may have one or more substituents.

<4> The process for producing an N-(hetero)aryl-substituted nitrogen-containing heteroaryl compound as described in <1> above, wherein the heteroaryl compound having an NH group as a ring-constituting component is indole which may have one or more substituents.

<5> The process for producing an N-(hetero)aryl-substituted nitrogen-containing heteroaryl compound as described in <1> above, wherein the (hetero)aryl compound having a leaving group is benzene, naphthalene, anthracene, phenanthrene, pyridine, pyridazine, pyrimidine, pyrazine, triazine, quinoline, isoquinoline, oxazole, benzoxazole, thiazole, benzothiazole, furan or benzofuran which may have one or more other substituents.

<6> The process for producing an N-(hetero)aryl-substituted nitrogen-containing heteroaryl compound as described in <1> above, wherein the (hetero)aryl compound having a leaving group is benzene or pyridine which each may have one or more other substituents.

<7> The process for producing an N-(hetero)aryl-substituted nitrogen-containing heteroaryl compound as described in <1> above, wherein the heterogeneous-system platinum group metal catalyst is palladium supported on carbon.

<8> The process for producing an N-(hetero)aryl-substituted nitrogen-containing heteroaryl compound as described in <1> above, wherein the ligand is a phosphine ligand.

<9> The process for producing an N-(hetero)aryl-substituted nitrogen-containing heteroaryl compound as described in <1> above, wherein the ligand is 1,1'-bis(diphenylphosphino)ferrocene (DPPF), 2,2'-bis(diphenylphosphino)-1,1'-binaphthyl (BINAP) or 2,2'-bis(diphenylphosphino)biphenyl ether (DPEphos).

Various techniques of reacting an aromatic amine with a halogenated aromatic compound using a palladium catalyst and a phosphorus ligand have been reported as methods of synthesizing aromatic amines (triarylamines) for use as charge-transporting agents in the fields of electrophotographic photoreceptors and organic electroluminescence (see, for example, JP-A-2004-307412 and JP-A-2005-145910). It should, however, be noted that these reactions basically differ from the reaction of the NH group as a heterocycle-constituting component in the invention. The reasons for this are as follows. The heteroaryl compound having an NH group as a ring-constituting component in the invention retains aromaticity because the lone pair of the nitrogen atom is conjugated with the heterocycle. Consequently, the proton of the NH group has a low pK$_a$ and is easily abstracted by a base to give an anion. This functions as a driving force in the reaction in the invention to yield a product in which the nitrogen atom on the heterocycle is directly bonded to a (hetero)aryl ring. In addition, the platinum group metal catalyst for use in the process of the invention, which is characterized by being a heterogeneous-system catalyst supported on carbon, silica gel, alumina, or the like, is effective in avoiding troubles accompanying the use of a homogeneous-system catalyst, such as the deterioration of product quality caused by metal inclusion, etc. and a troublesome operation for catalyst removal, to thereby enable a cost reduction in industrial production based on recovery and reuse.

DETAILED DESCRIPTION OF THE INVENTION

The invention will be explained below in detail.

The term "(hetero)aryl" means "aryl" or "heteroaryl".

One embodiment of the process of the invention will be described below in order to explain the process of the invention in more detail. However, the details of the invention should not be construed as being limited to those of the embodiment.

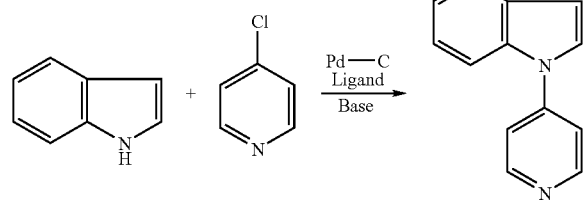

The heteroaryl compound having an NH group as a ring-constituting component to be used in the invention specifically is a 5- or 7-membered nitrogen-containing heteroaryl compound, which may be fused to another ring to form a fused ring. Preferred examples thereof include pyrrole, indole, pyrazole, indazole, imidazole, benzimidazole, triazole, and benzotriazole. More preferred are pyrrole, indole, imidazole, and benzimidazole. Especially preferred is indole.

Those heteroaryl compounds may have one or more substituents, and the substituents are not particularly limited. Preferred examples of the substituents include alkyl groups, alkenyl groups, alkynyl groups, aryl groups, a hydroxyl group, alkoxy groups, aryloxy groups, carbonyl groups, carbonyloxy groups, sulfonyl groups, amino groups, ureido groups, carbamoyl groups, carbonylamido groups, sulfamoyl groups, sulfonamide groups, a carboxy group, a sulfo group, a cyano group, halogen atoms, and heterocycle residues.

Examples of the (hetero)aryl compound having a leaving group to be used in the invention include benzene, naphthalene, anthracene, phenanthrene, pyridine, pyridazine, pyrimidine, pyrazine, triazine, quinoline, isoquinoline, oxazole, benzoxazole, thiazole, benzothiazole, furan, and benzofuran. Preferred are benzene and pyridine. More preferred is pyridine.

The leaving group possessed by the (hetero)aryl compound is not particularly limited. Preferred examples thereof include halogen atoms such as iodine, bromine, and chlorine; oxygen-atom-bonding type substituents such as sulfonyloxy groups (e.g., methylsulfonyloxy and trifluoromethylsulfonyloxy); and sulfur-atom-bonding type substituents such as alkylsulfonyl groups (e.g., methylsulfonyl and ethylsulfonyl) and arylsulfonyl groups (e.g., phenylsulfonyl and tosyl). More preferred are halogen atoms. Especially preferred is a chlorine or bromine atom.

The (hetero)aryl compound having a leaving group may have one or more other substituents, and the substituents are not particularly limited. Preferred examples of the substituents include alkyl groups, alkenyl groups, alkynyl groups, aryl groups, a hydroxyl group, alkoxy groups, aryloxy groups, carbonyloxy groups, a carboxyl group, carbonyl groups, sulfonyl groups, amino groups, ureido groups, carbamoyl groups, carbonylamido groups, sulfamoyl groups, sulfonamide groups, a sulfo group, a cyano group, halogen atoms, and heterocycle residues.

Specific examples of the N-(hetero)aryl-substituted nitrogen-containing heteroaryl compound which can be produced by the invention are shown below. However, the compound to be produced by the invention should not be construed as being limited to the following examples.

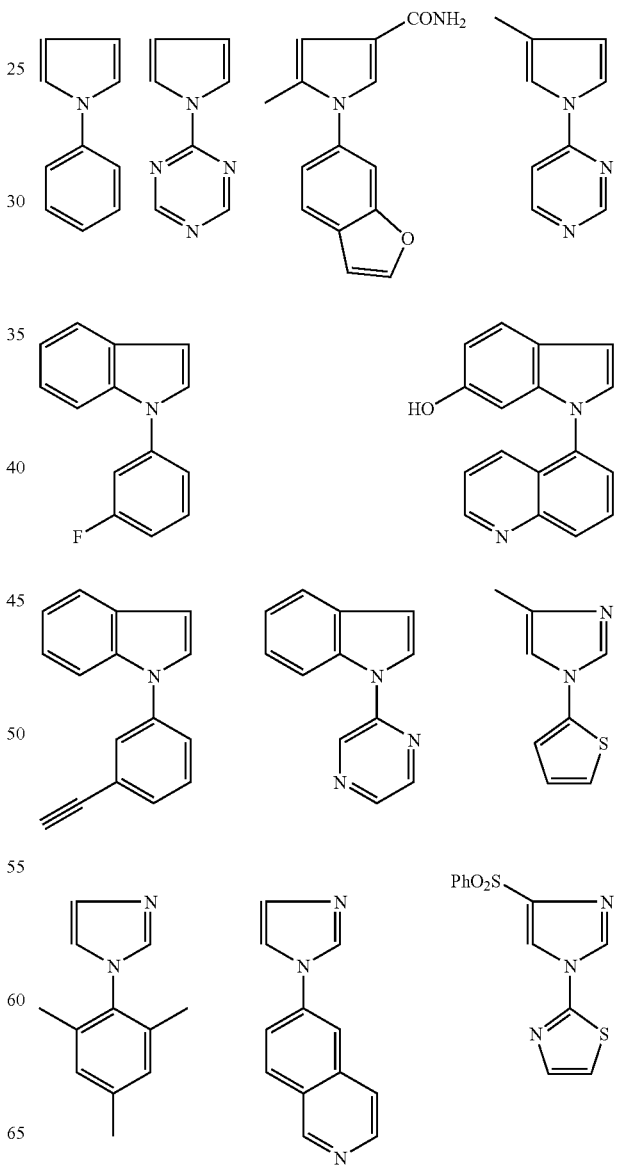

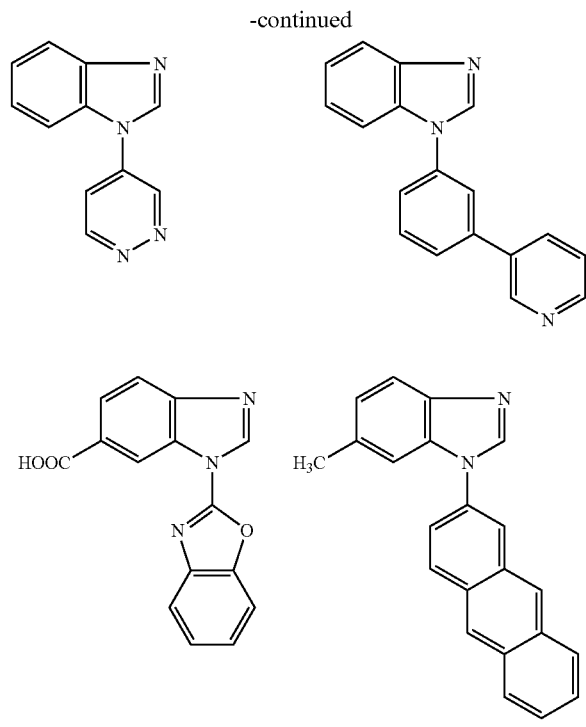
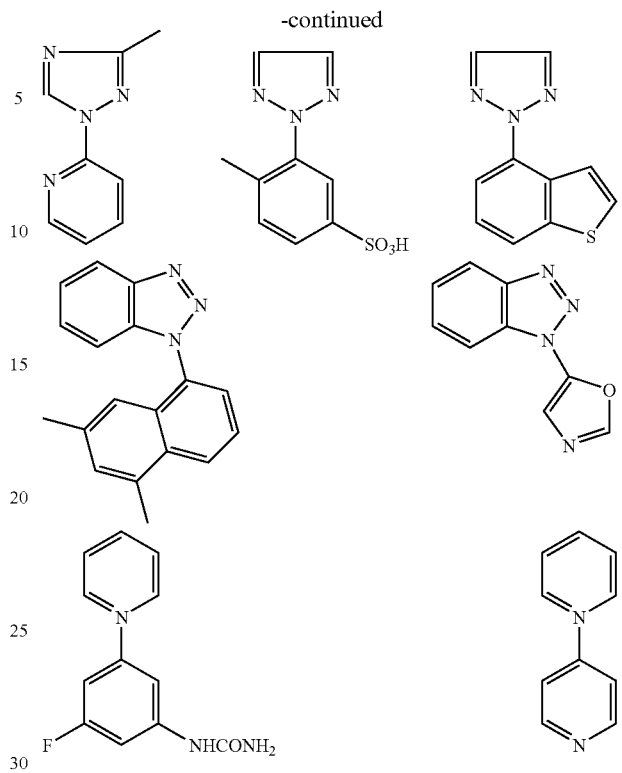
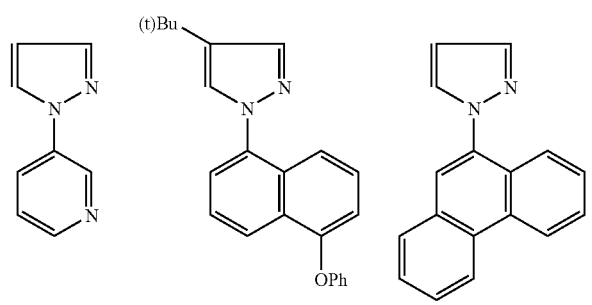
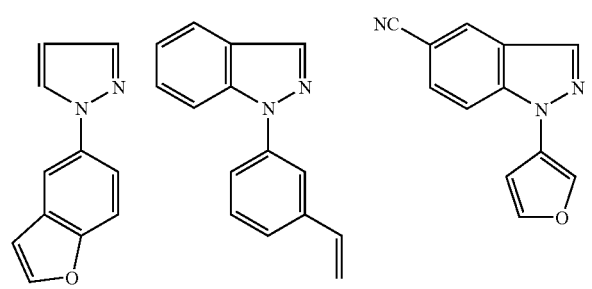
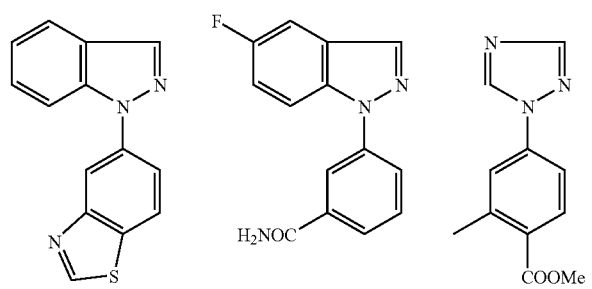

The process of the invention is explained next.

Many heteroaryl compounds having an NH group as a ring-constituting component which are usable in the invention are on the market and can be easily available.

Many (hetero)aryl compounds having a leaving group which are usable in the invention also are on the market and can be easily available. The amount of the (hetero)aryl compound having a leaving group to be used may be 0.5-2 equivalents to the heteroaryl compound having an NH group as a ring-constituting component. The amount thereof is preferably 0.8-1.5 equivalents, more preferably 0.9-1.2 equivalents, to the heteroaryl compound.

The heterogeneous-system platinum group metal catalyst to be used in the invention is a catalyst comprising a platinum group metal supported on a support. Examples of the platinum group metal include palladium, ruthenium, rhodium, osmium, iridium, and platinum. Preferred are palladium and platinum. More preferred is palladium. Examples of the support include carbon, silica gel, alumina, fibers such as silk fibroin, and beads of polystyrene having a phosphine ligand in a terminal group. These catalysts may be commercial ones, or may be prepared by known methods (e.g., *Shin Jikken Kagaku Kōza*, published by Maruzen Co., Ltd., 1977, Vol. 15, p. 390; and *Kōza Jūgo Hannō Ron*, published by Kagaku Dozin Co., Ltd., 1972, Vol. 10 (last volume), p. 355). Of these, palladium supported on carbon is especially preferred because it is easily available.

The amount of the heterogeneous-system platinum group metal catalyst to be used may be up to 20% by mole based on the heteroaryl compound having an NH group as a ring-constituting component. The amount thereof is preferably up to 5% by mole, more preferably up to 1% by mole, based on the heteroaryl compound.

The ligand to be used in the invention is not particularly limited as long as it is capable of coordinating to the heterogeneous-system platinum group metal catalyst. Preferred is a phosphine ligand. Preferred examples thereof include monophosphine ligands such as triphenylphosphine, triisopropylphosphine, tri-tert-butylphosphine, tricyclohexylphosphine, tri-o-tolylphosphine, and diphenylcyclohexylphosphine; and bisphosphine ligands such as 1,2-bis(di-tert-butylphosphino) ethane, 1,3-bis(diphenylphosphino)propane, 1,4-bis(diphenylphosphino)butane, 1,4-bis(di-tert-butylphosphino)butane, 1,2-bis(dicyclohexylphosphino)ethane, 1,1'-bis(diphenylphosphino)ferrocene (hereinafter abbreviated as DPPF), 2,2'-bis(diphenylphosphino)-1,1'-binaphthyl (hereinafter abbreviated as BINAP), and 2,2'-bis(diphenylphosphino)biphenyl ether (hereinafter abbreviated as DPEphos). More preferred of these are bisphosphine ligands. Even more preferred are DPPF, BINAP, and DPEphos.

The amount of the ligand to be used in the invention is preferably from 1:0.001 to 1:20, especially preferably from 1:0.01 to 1:4, in terms of the proportion of the metal atoms of the heterogeneous-system platinum group metal catalyst to the atoms coordinating thereto. For example, in the case where palladium supported on carbon and a bis-type phosphine ligand are used, the proportion of the palladium atoms to the phosphorus atoms is preferably from 1:0.001 to 1:20, especially preferably from 1:0.01 to 1:4.

The base to be used in the invention is one by which the NH group of the heteroaryl compound having an NH group as a ring-constituting component can be dissociated to yield a nitrogen anion. Examples thereof include inorganic bases such as sodium carbonate, potassium carbonate, sodium hydroxide, potassium hydroxide, and cesium carbonate; and metal alkoxides such as sodium methoxide, potassium methoxide, sodium tert-butoxide, and potassium tert-butoxide. Preferred are metal alkoxides. More preferred are sodium tert-butoxide and potassium tert-butoxide.

The amount of the base to be used varies depending on the kind of the base employed and the substituent to be dissociated. However, the amount thereof is generally 0.5-5 equivalents, preferably 0.8-4 equivalents, more preferably 1-3 equivalents, to the heteroaryl compound having an NH group as a ring-constituting component.

The reaction in the invention can be conducted without using any solvent. However, a solvent can be used according to circumstances. Examples of usable solvents include aromatic solvents such as toluene, xylene, and anisole; ether solvents such as tetrahydrofuran, 1,4-dioxane, ethylene glycol dimethyl ether, ethylene glycol diethyl ether, and diisopropyl ether; and amide solvents such as N,N-dimethylformamide, N,N-diethylformamide, N,N-dimethylacetamide, and N-methylpyrrolidone. These solvents may be used alone or as a mixture of two or more thereof. In the case of using a mixture of two or more solvents, the proportions thereof may be determined at will. The amount of the solvent to be used is not particularly limited. However, the amount thereof is preferably 0.1-100 times by mass, more preferably 1-50 times by mass, especially preferably 1.5-30 times by mass, the amount of the heteroaryl compound having an NH group as a ring-constituting component.

The reaction temperature in the invention is preferably 0-200° C., more preferably 10-150° C., especially preferably 20-120° C. The reaction time varies depending on the substrates, the catalyst used, etc. However, the disappearance of the starting materials is ascertained generally in 24 hours, mostly in 2-10 hours. It is preferred that the reaction in the invention be conducted in an atmosphere of an inert gas, e.g., nitrogen, argon, or helium.

After completion of the reaction, the N-(hetero)aryl-substituted nitrogen-containing heteroaryl compound obtained can be purified by an isolation/purification method for ordinary organic compounds. For example, the palladium-carbon in the liquid reaction mixture is filtered off, and water is added to the filtrate. The resultant liquid mixture is subjected to liquid separation and concentration, whereby a crude product is obtained. This crude product is further purified by recrystallization from ethyl acetate, toluene, an alcohol, hexane, etc., column purification with silica gel, vacuum distillation, etc. Such techniques may be used alone or in combination of two or more thereof to conduct purification, whereby the target compound having a high purity can be obtained.

EXAMPLES

The invention will be explained below in more detail by reference to Examples, but the invention should not be construed as being limited to the following Examples. Purity was evaluated by high-performance liquid chromatography (abbreviated as HPLC). Conditions for the HPLC are as follows: column, YMC-PACK ODS AM-312; detection UV, 254 nm; flow rate, 1.0 mL/min; eluent, acetonitrile/water (0.1% triethylamine+0.1% acetic acid)=1/1.

Example 1 Synthesis of 1-Pyridin-4-ylindole

In 600 mL of toluene were dissolved 30.0 g (0.20 mol) of 4-chloropyridine hydrochloride, 53.8 g (0.56 mol) of sodium t-butoxide, 19.6 g (0.01 mol) of 10 w/w % palladium-carbon (Pd—C) (containing 54 w/w % water), 23.4 g (0.20 mol) of indole, and 5.39 g (0.01 mol) of DPEphos. The resultant mixture was stirred for 10 hours with refluxing. After completion of the reaction, the reaction mixture was cooled to room temperature and the palladium-carbon was filtered off. This liquid reaction mixture was concentrated. 300 mL of ethyl acetate and 300 mL of 1-M hydrochloric acid were added to the residue to extract the target compound with the aqueous layer. Subsequently, 300 mL of ethyl acetate and 200 mL of 2-M aqueous sodium hydroxide solution were added to the aqueous layer to extract the target compound with the organic layer this time. This organic layer was washed with 200 mL of water and then dried with magnesium sulfate. The organic layer was filtered and concentrated to obtain 33.3 g (yield, 86%) of the target compound as an oily substance. The purity thereof was 99.8%.

Comparative Example 1 Synthesis of 1-Pyridin-4-ylindole

The target compound was synthesized by conducting the same procedure as in Example 1, except that the catalyst to be used was replaced by palladium acetate (Pd(OCOCH$_3$)$_2$) serving as a homogeneous-system catalyst and that the reaction conditions were changed as shown below.

The results obtained in Example 1 and Comparative Example 1 are shown in Table 1.

TABLE 1

| | Reagent | Reaction conditions | Yield (%) | Remarks |
|---|---|---|---|---|
| Example 1 | Pd—C DPEphos | refluxing 10 hr | 86 | heterogeneous-system reaction; catalyst recovery is possible |
| Comparative Example 1 | Pd(OCOCH$_3$)$_2$ DPEphos | refluxing 16 hr | 80 | homogeneous-system reaction; catalyst recovery is impossible |

The following are apparent from the results shown in Table 1.

The process of the invention can produce the target compound in a shorter reaction time than the other process and attains a satisfactory yield. Furthermore, the catalyst used can be recovered and repeatedly used. The target compound can hence be synthesized at a lower cost in the process of the invention than in the other process.

Examples 2 to 4

The same synthesis procedure as in Example 1 was conducted, except that the ligand to be used was replaced by those shown in Table 2.

Comparative Example 2

The same synthesis procedure as in Example 1 was conducted, except that no ligand was added.

The results obtained in the Examples and the Comparative Example are shown in Table 2.

TABLE 2

| Example | Ligand | Yield (%) |
|---|---|---|
| Example 1 | DPEphos | 86 |
| Example 2 | PPh$_3$ | 41 |
| Example 3 | BINAP | 80 |
| Example 4 | DPPF | 79 |
| Comparative Example 2 | no addition | reaction did not proceed |

Examples 5 to 8

The same synthesis procedure as in Example 1 was conducted, except that the substrates to be used were replaced by those shown in Table 3. The results obtained are shown in Table 3.

TABLE 3

| Example | Heteroaryl compound | (Hetero)aryl compound | Product | Yield (%) |
|---|---|---|---|---|
| 5 | 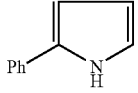 | 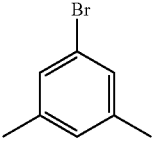 | 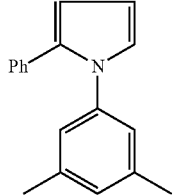 | 76 |
| 6 |  | 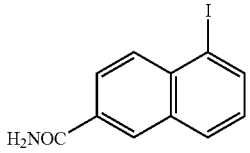 | 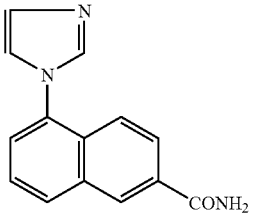 | 63 |
| 7 | 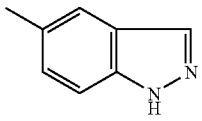 |  | 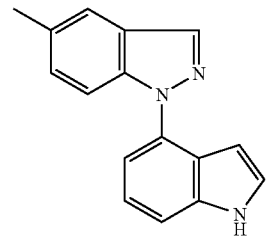 | 51 |
| 8 | 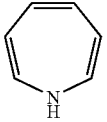 | 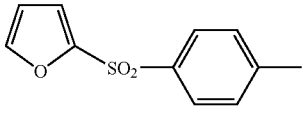 | 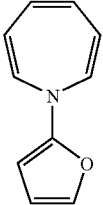 | 42 |

According to the invention, it has become possible to produce an N-(hetero)aryl-substituted nitrogen-containing heteroaryl compound useful for medicines, agricultural chemicals, organic electroluminescent elements, catalyst ligands and solar sell elements on an industrial scale in high yield at low cost.

The entire disclosure of each and every foreign patent application from which the benefit of foreign priority has been claimed in the present application is incorporated herein by reference, as if fully set forth.

What is claimed is:

1. A process for producing a pyridine-substituted indole ring wherein the pyridine ring is attached to ring nitrogen of the indole ring, the process comprising:
    reacting an indole, which may have one or more substituents, with pyridine having a leaving group, which may have one or more substituents, in the presence of a heterogeneous-system platinum group metal catalyst, a ligand and a base, wherein the heterogeneous-system platinum group metal catalyst is a catalyst comprising a platinum group metal supported on a support.

2. The process for producing a pyridine-substituted indole ring wherein the pyridine ring is attached to ring nitrogen of the indole ring according to claim 1,
    wherein the heterogeneous-system platinum group metal catalyst is palladium supported on carbon.

3. The process for producing a pyridine-substituted indole ring wherein the pyridine ring is attached to ring nitrogen of the indole ring according to claim 1,
    wherein the ligand is a phosphine ligand.

4. The process for producing a pyridine-substituted indole ring wherein the pyridine ring is attached to ring nitrogen of the indole ring according to claim 1,
    wherein the ligand is 1,1'-bis(diphenylphosphino)ferrocene (DPPF), 2,2'-bis(diphenylphosphino)-1,1'-binaphthyl (BINAP) or 2,2'-bis(diphenylphosphino)biphenyl ether (DPEphos).

5. The process for producing a pyridine-substituted indole ring wherein the pyridine ring is attached to ring nitrogen of the indole ring according to claim 1,
    wherein the platinum group metal is a metal selected from the group consisting of palladium, ruthenium, rhodium, osmium, iridium and platinum, and
    the support is a support selected from the group consisting of carbon, silica gel, alumina, fibers and beads of polystyrene having a phosphine ligand in a terminal group.

6. The process for producing a pyridine-substituted indole ring wherein the pyridine ring is attached to ring nitrogen of the indole ring according to claim 5, wherein the platinum group metal is palladium or platinum.

* * * * *